United States Patent [19]

Cahalan et al.

[11] Patent Number: 4,768,523
[45] Date of Patent: Sep. 6, 1988

[54] HYDROGEL ADHESIVE

[75] Inventors: Patrick T. Cahalan, Champlin; Allan H. Jevne, Anoka; Arthur J. Coury, St. Paul; Michael J. Kallok, New Brighton, all of Minn.

[73] Assignee: Lifecore Biomedical, Inc., Minneapolis, Minn.

[21] Appl. No.: 941,994

[22] Filed: Dec. 15, 1986

Related U.S. Application Data

[63] Continuation-in-part of Ser. No. 258,748, Apr. 29, 1981, abandoned.

[51] Int. Cl.$^4$ .............................................. A61N 1/05
[52] U.S. Cl. ................................ 128/785; 128/419 P; 252/315.1; 252/315.3
[58] Field of Search ................................ 128/639–641, 128/784, 785, 798, 802, 803, 419 P; 252/500, 315.1, 315.3; 106/205, 208

[56] References Cited

U.S. PATENT DOCUMENTS

| | | | |
|---|---|---|---|
| 3,587,565 | 6/1971 | Tatoian | 128/640 |
| 3,805,769 | 4/1976 | Sessions | 128/641 |
| 3,812,861 | 5/1974 | Peters | 128/798 |
| 3,815,611 | 6/1974 | Denniston, III | . |
| 3,840,520 | 10/1974 | Nordgren et al. | 252/315.3 |
| 3,911,906 | 10/1975 | Reinhold, Jr. | 128/641 |
| 3,994,302 | 11/1976 | Brennan | . |
| 3,998,215 | 12/1976 | Anderson et al. | 128/641 |
| 4,008,721 | 2/1977 | Burton | 128/802 |
| 4,016,869 | 4/1977 | Reichenberger | 128/640 |
| 4,066,078 | 1/1978 | Berg | 128/641 |
| 4,074,039 | 2/1978 | Lim et al. | . |
| 4,094,822 | 6/1978 | Kater | 252/512 |
| 4,125,110 | 11/1978 | Hymes | 128/641 |
| 4,141,366 | 2/1979 | Cross, Jr. et al. | . |
| 4,237,886 | 12/1980 | Sakurada et al. | 128/798 |
| 4,273,135 | 6/1981 | Larimore et al. | 128/640 |
| 4,282,886 | 8/1981 | King | 128/419 P X |
| 4,299,231 | 11/1981 | Karmann et al. | 128/639 |
| 4,352,359 | 10/1981 | Larimore et al. | 128/640 |
| 4,391,278 | 7/1983 | Cahalan et al. | 128/640 |
| 4,406,827 | 9/1983 | Carim | 128/639 X |
| 4,524,087 | 6/1985 | Engel | 427/2 |
| 4,539,996 | 9/1985 | Engel | 128/640 |

FOREIGN PATENT DOCUMENTS

0012402 6/1980 European Pat. Off. ............ 128/639
2842318 4/1980 Fed. Rep. of Germany .

OTHER PUBLICATIONS

"New Pacemaker Electrodes", Transactions: American Society Artificial Internal Organs, vol. 29, pp. 29–35, 1971.
"Hydrogels—A Broad Class of Biomaterials", A. S. Hoffman, Polymers in Medicine and Surgery, pp. 33–44.
"Use of Biological Glue in Acute Aortic Dissection", D. Guilmet, et al., The Jour. Thoracic and Cardiovascular Surgery, vol. 77, No. 4, (Apr. 1979), pp. 516–521.
"The Use of Crosslinked Gelatin as a Tissue Adhesive to Control Hemorrhage from Liver and Kidney", C. J. Tatooles et al., Surgery, vol. 60, No. 4, pp. 857–861, (Oct. 1966).
"Surgical Adhesives and Coatings", P. Y. Wang, Medical Eng., pp. 1123–1130.
"The Effect of the Physiological Environment on the Mechanical Properties of Biomaterials in Cardiovascular Applications", S. D. Bruck, Biomat. Med. Dev., Art. Org., 6(4), 341–359, (1978).
"Interactions of Synthetic and Natural Surfaces with Blood in the Physiological Environment", S. D. Bruck, J. Biomed. Mater. Res. Symposium, No. 8, pp. 1–21, 1977.
"Biocompatibility Testing of Polymers: In Vivo Implantation Studies", S. J. Gourlay, et al., J. Biomedical Materials Research, vol. 12, 219–232, (1978).
"Materials for Use in the Eye", M. F. Rofojo, Polm. Sci. Tech., vol. 8, pp. 313–331, (1975).
"Characterization of Graft Polymers for Biomedical Applications", B. D. Ratner, J. Biomed. Materials Research, vol. 14, pp. 665–687, (1980).

Primary Examiner—Lee S. Cohen
Attorney, Agent, or Firm—Oliver F. Arrett

[57] ABSTRACT

An improved hydrogel adhesive, particularly adapted for adhesion and contact to tissue. It is especially useful in attaching electrical leads to tissue, for example in attaching pacemaker leads to the heart, interiorly or exteriorly.

7 Claims, 1 Drawing Sheet

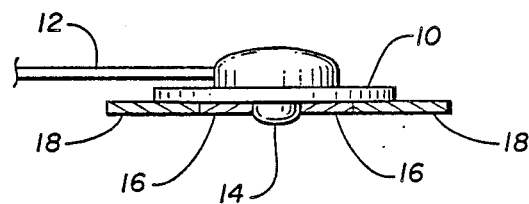
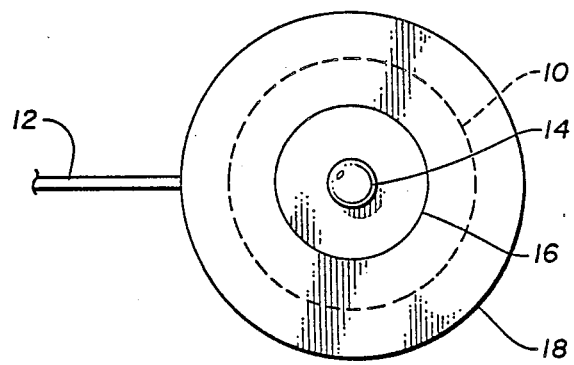

HYDROGEL ADHESIVE

Background of Prior Art

This is a continuation-in-part application based on parent application Ser. No. 258,748, filed Apr. 29, 1981, now abandoned.

DESCRIPTION

Alkyl cyanoacrylates have found use as tissue adhesives. These materials have also been considered for use as an adhesive for attaching electrode leads to tissue. For example, a specific use considered has been with cardiac pacing leads for facilitating lead attachment to the heart, either to the epicardium or the endocardium. Previously, such leads were attached by suturing or with helical coils. However, these techniques are sometimes unacceptable because of various associated trauma. The poly-alkyl cyanoacrylates may degrade to form undesirable by-products.

Hydrogels constitute a broad class of materials which swell extensively in water but are not completely water soluble. They have been used in a variety of biomedical applications and may be applied in bulk forms which vary from clear to opaque and from a relatively stiff to a relatively soft consistency. Sometimes the bulk forms are reinforced by woven fabrics to increase the composite strength. Hydrogels have also been used as coatings for various biomedical applications.

BRIEF SUMMARY OF THE INVENTION

It has been discovered that partially dehydrated hydrogels, in which the hydrogel polymers contain controlled cross-linking, exhibit excellent adhesive properties, particularly in attaching to moist body tissue. The adhesive qualities of the hydrogels are affected by the degree of water content of the hydrogel. Aggressive adhesion develops during the initial phase of tissue contact when the hydrogel is hydrating or rehydrating.

Although many adhesive applications, particularly those involving tissue, are included within the purview of the hydrogel compositions of this invention, a preferred use is found as an adhesive for attaching pacing leads to heart tissue, particularly epicardial tissue and other moist internal tissue.

BRIEF DESCRIPTION OF THE DRAWINGS

FIGS. 1 and 2 are top and bottom views, respectively, of a schematic showing of a epicardial pacing lead incorporating the adhesive composition of the invention.

DETAILED DESCRIPTION OF THE INVENTION

As already noted the term "hydrogel" refers to a wide variety of polymer-based compositions. These materials may be synthesized for example from monomer(s) or from monomer(s) mixed with polymer(s) in water. They may be obtained by chemical modification of existing polymer(s) or by adding water to existing dry polymers.

Generally speaking, a hydrogel according to the invention will comprise a coherent, three-dimensional aqueous polymer system capable of imbibing water without liquefying. Usually, insolubility in water is provided by crosslinking the hydrogel polymer. Hydrogels or water-containing gels of the invention may be comprised of water and various chemical substances including gelatin; polysaccharides; crosslinked acrylamide polymers, hydroxyethylmethacrylate polymers; crosslinked polyhydroxyethylacrylate; polymerized, crosslinked 2-acrylamido-2-methylpropane sulfonic acid polymers or one of their salts such as the sodium or potassium type; crosslinked polyvinylpyrrolidone; polyacrylic acid; copolymers of the aforementioned monomers with each other, and copolymers of the aforementioned monomers with other polymers such as polystyrene or other non-hydrogel-forming polymers.

For example, by cross-linking homopolymers (as with methylenebis-acrylamide) of an acrylamide derivative such as 2-acrylamido-2-methylpropanesulfonic acid or one of its salts form hydrogels may be formed. Co-polymers thereof may also be formed in the same way with acrylamide. Cross-linked homopolymers of acrylic acid and of methacrylic acid, their salts and copolymers thereof do likewise, as do other acrylic cross-linked homopolymers and copolymers.

Hydrogels of this invention derive their adhesive properties in part from their ability to absorb water. When a relatively dry body of hydrogel contacts moisture, such as the moisture in tissue, particularly internal tissue, or any other moist surface, it develops an aggressive adhesive nature. When the polymer of the hydrogel is crosslinked to an adequate degree, bulk hydrogel is strong enough, even when swelled with additional liquid, to provide adhesive support for pacing leads, thereby establishing extended connection of the lead to tissue e.g., for a period of time long enough for fibrotic tissue to fix the lead in position.

Excessive crosslinking decreases the tack of the hydrogel. Too little crosslinking decreases its cohesive strength. Crosslinking agent content up to about 0.4 equivalent % are satisfactory in the polymer of the hydrogels of this invention.

According to the invention, the hydrogel is dried so as to contain a controlled amount of about 70 to about 98% polymer by weight, balance water. That is, the hydrogel is dried following its preparation to remove a predetermined amount of the water contained by the gel leaving a higher amount of polymer in the gel relative to its water content. As prepared, hydrogels may ordinarily contain about 20–65% polymer, balance water.

Preferred examples are described below.

EXAMPLE I 66 grams of 2-acrylamido-2-methylpropane sulfonic acid monomer were mixed with 46 grams of distilled water and 10 mls of a 1% aqueous solution of methylene-bis-acrylamide. This solution was deaerated and 1 cc each of 0.38% potassium bisulfite, 0.38% potassium persulfate, and 0.24% ferrous sulfate solutions were added simultaneously. The resultant solution was cast into sheet form under nitrogen and allowed to solidify. The resulting gel was dried at 60° C. overnight in a forced air oven to an extent such that the dried gel contained from about 2 to 30% water by weight. A preferred final water content of the hydrogel is about 20% by weight. In the dried state the resultant gel was a clear, somewhat stiff material and, upon contact with a moist surface such as epicardial tissue, it formed a quick and firm adhesive bond.

EXAMPLE II 43 grams of 2-acrylamido-2-methylpropane sulfonic acid monomer and 23 grams of acrylamide were mixed with 44 grams of distilled water. 8 mls of 1% methylene-bis-acrylamide were added and the solution was deaerated and initiated with reagents described in Example I. This gel was dried similarly and the resulting product also formed a strong adhesive bond to a moist surface.

EXAMPLE III

Copolymer Gel 43 grams of 2-acrylamido-2-methylpropane sulfonic acid monomer were mixed with 23 grams of acrylic acid and 44 grams of distilled water. 10 mls of a 1% aqueous methylenebis-acrylamide solution were added and the solution was deaerated and initiated as in the above Examples. Again, the dried gel was within the previously mentioned water content range and showed adhesive bonding properties when brought into contact with a moist surface.

EXAMPLE IV 40 grams of acrylic acid were mixed with 60 grams of water and 2 mls. of a 1% solution of methylene-bis-acrylamide (MBA), a cross-linking agent. 0.6 grams of a 33% solution of ammonium persulfate were added as an initiator. The resultant solution was cast into sheet form and placed in a vacuum oven where it was evacuated and released to nitrogen twice. The system was heated at 60° C. overnight in a nitrogen atmosphere to produce a hydrogel formed. The resultant medium-hard gel contained only about 10% water and exhibited rapid adhesion to moist surfaces.

EXAMPLE V

Polymer Blend 20 grams of a 50% solution of polyacrylic acid in water (Goodrite K732, B. F. Goodrich Chemical Division) were mixed with 5 grams of hydroxyethylmethacrylate (HEMA) and 2 grams of a 0.6% azobisisobutyronitrile (AIBN) solution in HEMA. The resultant gel was dried as in Example IV and exhibited good adhesiveness, low swelling and good cohesive strength.

Referring now to the Figures, a preferred use of the hydrogel compositions of the invention is in a pacing lead of the epicardial type as shown in FIG. 1. The lead comprises a base or support member 10 of a polymer insulating material such as silicone or polyurethane, carrying an electrical lead 12. Lead 12 is connected to an electrode 14 which may or may not be exposed on the bottom of base 10 as shown to electrically contact tissue. If not exposed, electrical contact is through the hydrogel 16, now to be described. Base 10 carries on its bottom an attached film or thin layer of hydrogel 16 prepared according to the invention. Film or layer thicknesses, for example, can typically be about 0.040–0.060 inches, although this is not critical and may vary widely. Attachment may be by means of an adhesive or mechanical interlock. If the electrode is prepared using extensively dried hydrogel (water content to be adjusted later), the film may not have pressure sensitive adhesive properties, and, an adhesive or mechanical interlocking arrangement may be used to attach the hydrogel to the base member. However, if the electrode is prepared with the hydrogel in its adhesive condition i.e., having a small controlled predetermined water content, the natural adhesiveness of the hydrogel is adequate for attachment to the base member. In such a case, the electrode would have to be sealed to prevent evaporation until its use. Hydrogel 16 is positioned on base 10 as shown so as to contact tissue when the base is laid on same. A Dacron patch 18 may be interposed between support 10 and film 16. It may be attached by an adhesive or any other means to base 10 and the hydrogel 16 to enhance fibrotic encapsulation for chronic fixation. Preferably, such a patch will extend (not shown) beyond the edges of the hydrogel to facilitate fibrotic capture. It may also be used to provide mechanical attachment of the hydrogel to the base if the hydrogel is being used in a dried condition.

The patch material may be any polyester other than Dacron and may also be of polyethylene, polypropylene and polytetrafluoroethylene or other materials as well. One example of such mesh fabrics is the Monodur ® screen fabric line available from Industrial Fabrics Corporation, 7208 Boone Avenue North, Minneapolis, Minn. 55428. A typical example of the mesh opening size will be between about 80 and 400 microns, although this is not critical.

Many changes in configuration will be apparent without departing from the scope of the invention. The description herein is not intended to be limiting. The exclusive property rights are defined below.

What is claimed is:

1. A self-supporting hydrogel adhesive body consisting essentially of predetermined relative amounts of hydrogel polymer and water, the hydrogel polymer ranging from about 70% to about 98% by weight of hydrogel, balance consisting essentially of water, the polymer additionally containing an amount of a cross-linking agent ranging up to about 0.4 equivalent percent.

2. The adhesive body of claim 1 wherein the polymer consists essentially of polymerized 2-acrylamido-2-methylpropanesulfonic acid or one of its salts.

3. The adhesive body of claim 1 wherein the polymer comprises copolymerized 2-acrylamido-2-methylpropanesulfonic acid or one of its salts and acrylamide.

4. The adhesive body of claim 1 wherein the polymer comprises copolymerized 2-acrylamido-2-methylpropanesulfonic acid or one of its salts and acrylic acid.

5. The adhesive body of claim 1 wherein the polymer comprises polymerized acrylic acid.

6. The adhesive body of claim 1 wherein the polymer comprises polymerized methacrylic acid.

7. The adhesive body of claim 1 wherein the polymer comprises copolymerized acrylic acid and methacrylic acid.

* * * * *

UNITED STATES PATENT AND TRADEMARK OFFICE
CERTIFICATE OF CORRECTION

PATENT NO. : 4,768,523

DATED : September 6, 1988

INVENTOR(S) : Patrick T. Cahalan et al.

It is certified that error appears in the above-identified patent and that said Letters Patent is hereby corrected as shown below:

On the title page, Item [73] should read

-- [73] Assignee: Medtronic, Inc., Minneapolis, Minn. --.

Signed and Sealed this

First Day of August, 1989

Attest:

*Attesting Officer*

DONALD J. QUIGG

*Commissioner of Patents and Trademarks*